(12) United States Patent
Karmalawy

(10) Patent No.: US 6,446,286 B1
(45) Date of Patent: Sep. 10, 2002

(54) PATIENT SUPPORT TABLE FOR MEDICAL IMAGING HAVING REGIONS FOR REDUCED RADIATION ATTENUATION

(75) Inventor: Moataz Karmalawy, San Ramon, CA (US)

(73) Assignee: Koninklijke Philips Electronics N.V. (NL)

( * ) Notice: Subject to any disclaimer, the term of this patent is extended or adjusted under 35 U.S.C. 154(b) by 0 days.

(21) Appl. No.: 09/499,261

(22) Filed: Feb. 7, 2000

(51) Int. Cl.[7] .......................... A61G 13/00; A61G 7/00
(52) U.S. Cl. ........................... 5/601; 600/425; 600/436; 600/407; 378/208; 378/209
(58) Field of Search .................... 5/601, 600; 600/407, 600/436, 425; 378/208, 209

(56) References Cited

U.S. PATENT DOCUMENTS

| | | | | |
|---|---|---|---|---|
| 3,165,630 A | * | 1/1965 | Bielat et al. ................... | 5/601 |
| 4,103,170 A | * | 7/1978 | Spradlin ........................ | 5/601 |
| 4,527,787 A | * | 7/1985 | Collis, Jr. ..................... | 5/601 |
| 5,987,672 A | * | 11/1999 | Oosterwaal .................... | 5/601 |

* cited by examiner

Primary Examiner—Alexander Grosz
(74) Attorney, Agent, or Firm—Eugene E. Clair

(57) ABSTRACT

The present invention describes an apparatus for an improved patient support table for use in nuclear medical studies. The table provides regions, such as a slot or hole, where there is lowered radiation attenuation for particular regions of the body. By supporting and aligning the patient with these regions of lowered radiation attenuation, better image quality and/or lowered radiation dosage may be achieved.

16 Claims, 4 Drawing Sheets

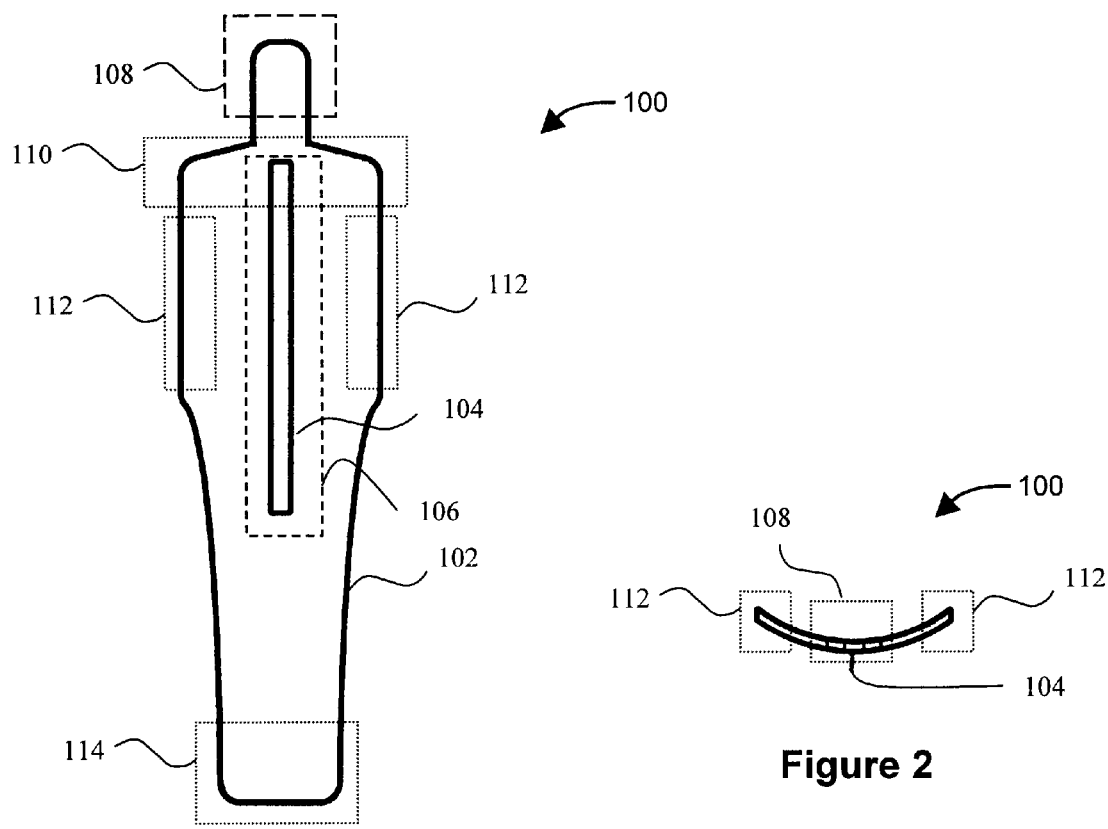
Figure 1
Figure 2
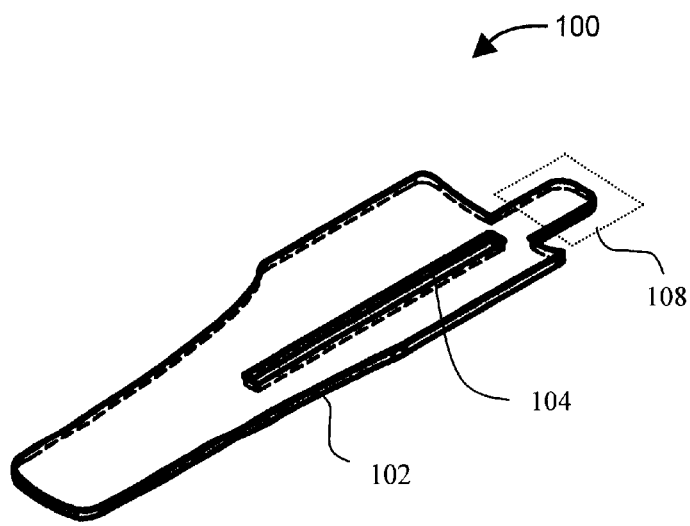
Figure 3

PATIENT SUPPORT TABLE FOR MEDICAL IMAGING HAVING REGIONS FOR REDUCED RADIATION ATTENUATION

FIELD OF THE INVENTION

The present invention pertains to the field of nuclear medicine. More particularly, the present invention relates to a patient support mechanism for nuclear medicine and imaging studies.

BACKGROUND OF THE INVENTION

In nuclear medicine, images of internal structures or functions of the body are acquired by detecting gamma radiation that is emitted from within the body or transmitted through the body. A factor affecting the quality of the acquired images is attenuation of the radiation between the source and the detector. There are various potential sources of attenuation of the radiation, one being structures within the body, and another being the patient support table. In nuclear medicine, it is common to detect radiation by positioning the detectors at various different angles about the patient's body. Consequently, in certain instances, the table may be between a given detector and the patient's body, thereby causing attenuation of radiation reaching that detector. Previous patient support tables provided basic support for the patient but also undesirably attenuated the radiation from the source to the detector. Additionally, the earlier approaches required the purchase of separate accessories for certain needs. Such accessories might include armrests, head support, etc.

Thus, it is desirable to provide a patient support mechanism with lowered attenuation compared to the previous approaches, while at the same time providing features that were previously available only by adding accessories.

SUMMARY OF THE INVENTION

An improved patient support table for medical imaging studies is disclosed. The table has regions where radiation attenuation is lower than that of surrounding regions of the table. The table facilitates acquisition of radiation passing through the lowered attenuation region. The table may also have contours to assist in supporting and aligning the patient with the region of lowered radiation attenuation. Because of the lowered attenuation it may be possible to reduce the total radiation dosage for a given medical image quality and/or reduce radiation damage to the patient.

Other features of the present invention will be apparent from the accompanying drawings and from the detailed description that follows.

BRIEF DESCRIPTION OF THE DRAWINGS

The present invention is illustrated by way of example and not limitation in the figures of the accompanying drawings, in which like references indicate similar elements and in which:

FIG. 1 is a top view of one embodiment of the patient support.

FIG. 2 is an end section view of the patient support shown in FIG. 1.

FIG. 3 is a perspective view of the patient support shown in FIG. 1.

DETAILED DESCRIPTION

Figure 4:
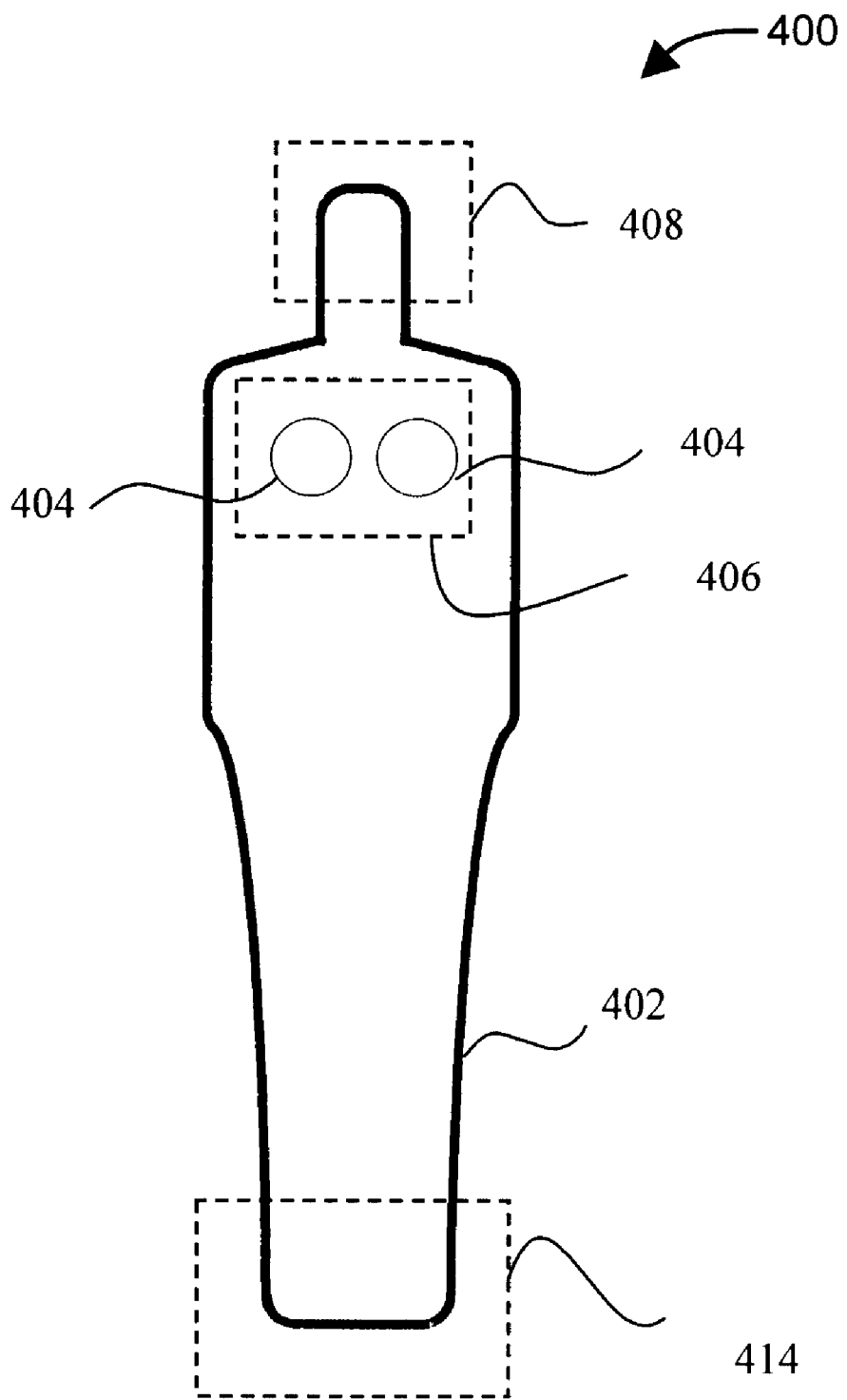
FIG. 4 is a top view of one embodiment of the patient support.

An improved patient support table with lowered radiation attenuation at specified regions for use in nuclear medicine is described. The support mechanism, by performing patient support while providing lowered attenuation of diagnostic radiation, may allow for better resolution, higher accuracy, or lowered radiation dosage, to achieve a desired detail for a diagnostic study. By providing a slot in the table for spine, and/or holes in the table for breast imaging, radiation attenuation by the table is substantially reduced in these regions.

FIG. 1 illustrates a top view of the table 100 for one embodiment shown without supporting members. In FIG. 1, the outline of the table 102 follows the general outline of the human body and is indicative of how the patient might be positioned for imaging, with the head in the head region 108, the shoulders in the shoulder region 110, the arms in the arm regions 112, and the feet toward the foot section 114. The slot 104 in table 100 is located where the patient's spine will be located and is sized and shaped approximately like a typical human spine. Slot 104 represents the boundary of a region of the table 100 where there is lowered attenuation 106. In one embodiment, the region of lowered attenuation 106 may be an opening in the table 100. Such an opening may be a slot, which may be desirable for studies in the spine area, whereas holes may be particularly useful for breast scans. Other apertures may be tailored for particular needs, such as cardiac studies. The region of lowered attenuation 106 may consist of a groove, hollow, or indentation in the table. Alternatively or additionally, the region of lowered attenuation 106 might include materials that have a lower attenuation than the surrounding materials. By including the region of lowered radiation attenuation, it may be possible to reduce the dosage of radiation needed to achieve a given image quality. This possible reduction in dosage may reduce radiation damage to the patient's body.

FIG. 2 illustrates an end view according to one embodiment where the patient table 100 in FIG. 2 is non-planar. This curvature assists in providing alignment of the patient with the lowered attenuation region, patient stability, and patient comfort. Additionally the curvature may provide an integrated arm support mechanism in the arm regions 112. Likewise, curvature in the head region 108 may provide built-in head support.

FIG. 3 illustrates a perspective view of one embodiment, in which the lowered attenuation region 106 in FIG. 1 is a slot along the spinal region of a patient positioned as described above in the FIG. 1 description. FIG. 4 illustrates a top view of the table 400 for one embodiment shown without supporting members. In FIG. 4, the outline of the table 402 follows the general outline of the human body and is indicative of how the patient might be positioned for imaging, with the head in the head region 408, and the feet toward the foot section 414. The holes 404 are located where the patient's breasts will be located and are sized and shaped to accommodate a typical human breast when the patient lies on her stomach. Hole 404 represents the boundary of a region of the table 400 where there is lowered attenuation 406. The region of lowered attenuation 406 may consist of an opening in the table 400, a groove, hollow, or indentation in the table 400, or might include materials that have a lower attenuation than the surrounding materials.

Figure 5:
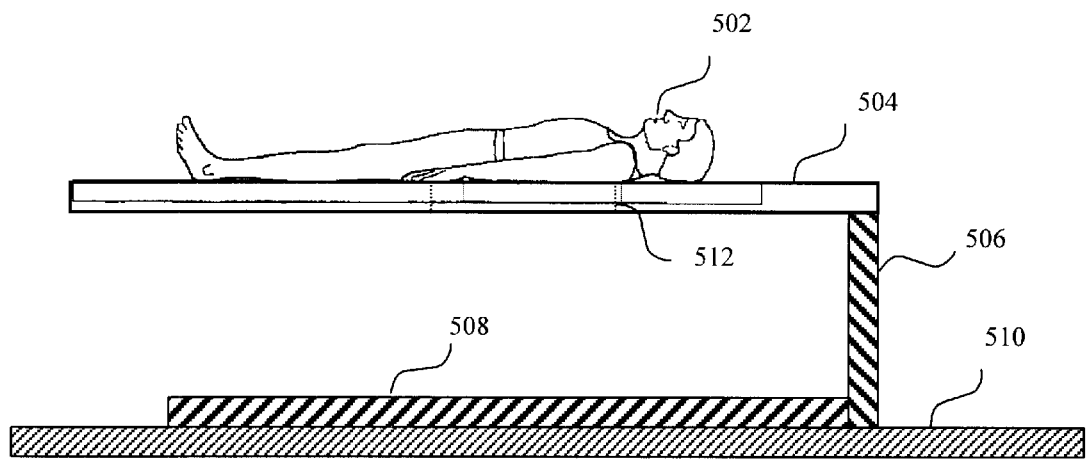
FIG. 5 is a side view of one embodiment of the patient support illustrating a cantilever support mechanism.
Figure 6:
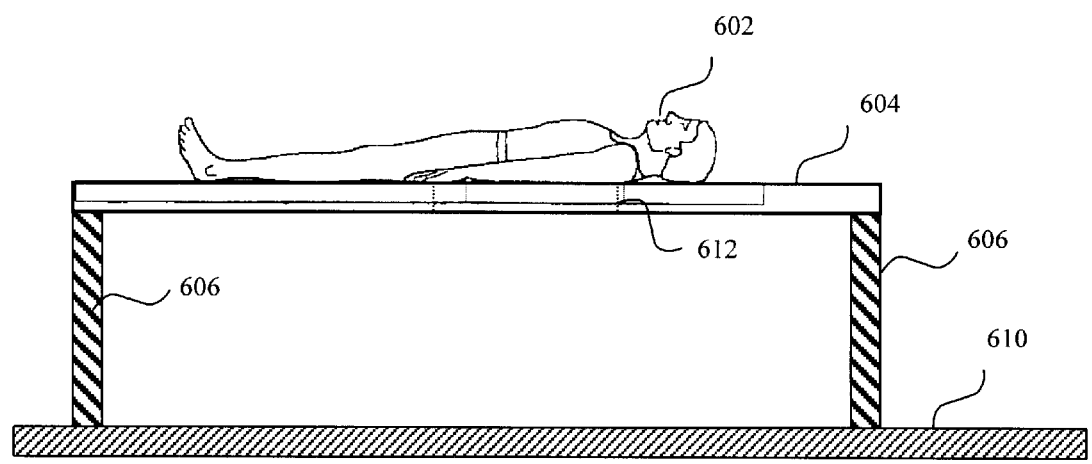
FIG. 6 is a side view of one embodiment of the patient support illustrating a dual support mechanism.

FIG. 5 illustrates a side view of one embodiment where the patient 502 is being supported on the table 504 which is held in place by the cantilever support mechanism comprising the vertical cantilever support member 506 and the base support member 508 which is resting upon the floor 510. FIG. 6 illustrates a side view of one embodiment where the patient 602 is being supported on the table 604 which is held in place by the dual support members 606 which are resting upon the floor 610. Both the embodiments described in FIG. 5 and FIG. 6 are advantageous to allow radiation detectors and/or emitters to be rotated around the patient under the table 504, 604, as shown in FIG. 7.

Figure 7:
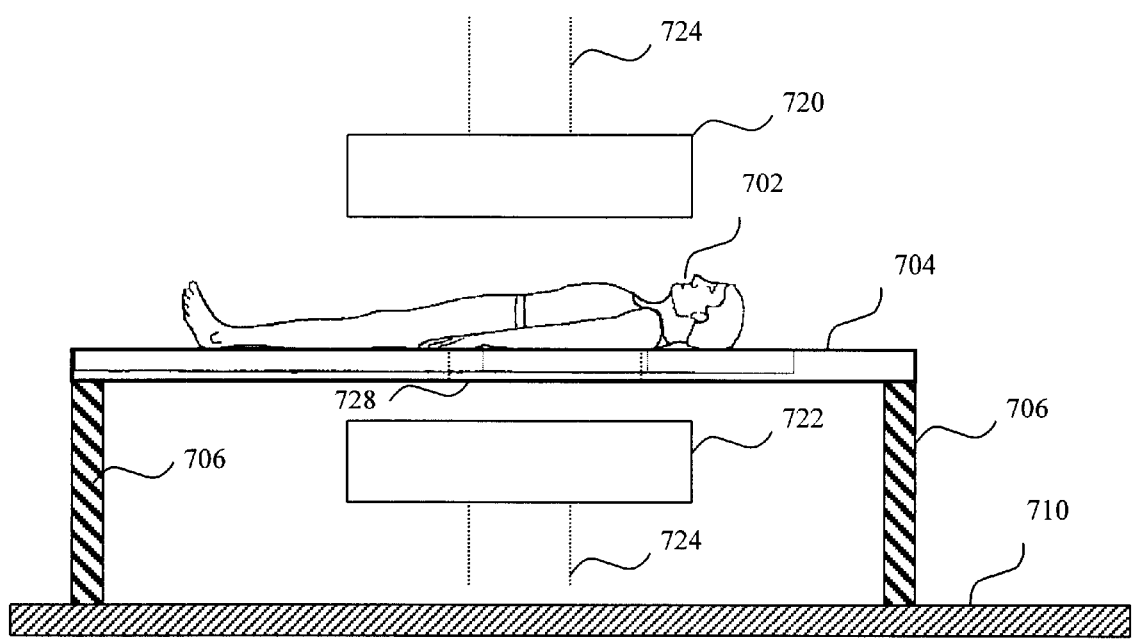
FIG. 7 is a side view of one embodiment of the patient support illustrating use with an imaging system.

FIG. 7 illustrates a side view of one embodiment of the table used with a medical imaging system. The patient 702 is being supported on the table 704 which is held in place by the dual support members 706 which are resting upon the floor 710. The medical imaging system might comprise a gantry 724 and a top radiation detector 720 and a bottom radiation detector 722.

Thus, what has been described above is a patient support mechanism which provides lowered attenuation in regions of medical imaging interest, while at the same time providing integrated support and alignment. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A patient support table for medical imaging studies having a first region therein for which radiation attenuation is lower than radiation attenuation of at least one adjacent region of the patient support table, such that more radiation can pass through said region of lowered attenuation than can pass through said at least one adjacent region of the patient support table, the first region positioned to increase radiation transmission of a corresponding region of the body of the patient relative to the at least one adjacent region.

2. The apparatus according to claim 1, wherein said region of lowered radiation attenuation comprises an opening in the table.

3. The apparatus according to claim 1, wherein said region of lowered radiation attenuation comprises a reduced thickness in the table as compared with said surrounding regions of the table.

4. The apparatus according to claim 1, wherein said region of lowered radiation attenuation comprises a different material as compared with said surrounding regions of the table.

5. The apparatus according to claim 1, wherein said region of lowered radiation attenuation is located so as to be aligned with the spine of a patient.

6. The apparatus according to claim 1, wherein said region of lowered radiation attenuation is located so as to be aligned with a breast of a patient.

7. An apparatus for supporting a patient for a medical imaging study comprising:

a patient support member;

a support member holding the patient support member in place; and a region of lowered attenuation included within the patient support member, such that more radiation can pass through said region of lowered attenuation than can pass through at least one adjacent region of the patient support member, positioned to improve imaging of a corresponding region of the body of the patient.

8. The apparatus according to claim 7, wherein the support member holding the patient support member in place is configured in such a manner as to allow radiation detectors and/or emitters to be rotated around patient support member.

9. The apparatus according to claim 7, wherein the support member holding the patient support member in place comprises a cantilever support mechanism.

10. The apparatus according to claim 7, wherein the support member holding the patient support member in place comprises a dual support mechanism attached to opposing ends of the patient support member.

11. The apparatus according to claim 7, wherein the region of lowered attenuation comprises an opening in the patient support member.

12. The apparatus according to claim 7, wherein the region of lowered attenuation comprises a reduced thickness of the patient support member as compared with the at least one adjacent region of the patient support member.

13. The apparatus according to claim 7, wherein the region of lowered attenuation included within the patient support member comprises a different material than that of the at least one adjacent region of the patient support member.

14. The apparatus according to claim 7, wherein the region of lowered attenuation comprises an opening in the support member holding the patient support member in place.

15. The apparatus according to claim 7, wherein the patient support member comprises one or more curved surfaces.

16. An apparatus comprising:

means for supporting a patient during medical imaging, said means for supporting including a region of lowered radiation attenuation; and means for aligning the patient with said region of lowered attenuation, such that more radiation can pass through said region of lowered attenuation than can pass through at least one adjacent region of said means for supporting the patient, positioned to improve imaging of a corresponding region of the body of the patient.

* * * * *